United States Patent
Prato

(10) Patent No.: US 8,551,498 B2
(45) Date of Patent: *Oct. 8, 2013

(54) **SOLID COMPOSITION CONTAINING *BACILLUS*-TYPE NON-PATHOGENIC BACTERIAL SPORES**

(75) Inventor: Tiziano Prato, Varese (IT)

(73) Assignee: Sanofi-Aventis S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/234,424

(22) Filed: Sep. 16, 2011

(65) Prior Publication Data

US 2012/0009167 A1   Jan. 12, 2012

Related U.S. Application Data

(63) Continuation of application No. 10/484,937, filed as application No. PCT/EP02/08384 on Jul. 26, 2002, now Pat. No. 8,039,006.

(30) Foreign Application Priority Data

Jul. 27, 2001  (IT) .............................. MI2001A1632

(51) Int. Cl.
| | |
|---|---|
| *A61K 39/07* | (2006.01) |
| *A61K 39/00* | (2006.01) |
| *A61K 39/38* | (2006.01) |
| *A61K 45/00* | (2006.01) |
| *A61K 47/00* | (2006.01) |
| *A01N 63/00* | (2006.01) |
| *A01N 65/00* | (2009.01) |
| *C12P 1/00* | (2006.01) |

(52) U.S. Cl.
USPC ................ 424/246.1; 424/184.1; 424/278.1; 424/93.1; 424/93.46; 435/41

(58) Field of Classification Search
None
See application file for complete search history.

(56) References Cited

U.S. PATENT DOCUMENTS 6,924,133 B1 *  8/2005  Jørgensen et al. ............ 435/187

FOREIGN PATENT DOCUMENTS

WO      WO 99/49877      * 10/1999

OTHER PUBLICATIONS

International Search Report for WO03011341 dated Feb. 13, 2003.

* cited by examiner

*Primary Examiner* — Vanessa L. Ford
*Assistant Examiner* — Lakia Tongue
(74) *Attorney, Agent, or Firm* — Lathrop & Gage LLP; James H. Velema, Esq.

(57) ABSTRACT

The invention relates to a composition of spores of nonpathogenic bacteria of the *Bacillus* genus, adsorbed onto a matrix made up of at least one water-insoluble adsorbent compound and a cellulose derivative, which can be obtained by the fluidized air bed technique, useful in the pharmaceutical, veterinary and nutrition fields.

16 Claims, No Drawings

SOLID COMPOSITION CONTAINING *BACILLUS*-TYPE NON-PATHOGENIC BACTERIAL SPORES

RELATED APPLICATIONS

This application is a continuation of U.S. application Ser. No. 10/484,937, now U.S. Pat. No. 8,039,006, which is a §371 national-stage application of International PCT application no. PCT/EP02/08384, filed Jul. 26, 2002, which claims priority to Italian application no. 12001A001632, filed Jul. 27, 2001.

The present invention relates to a solid composition containing spores of nonpathogenic bacteria, for use in the pharmaceutical, veterinary or nutrition fields, in particular to a composition containing spores of bacteria of the *Bacillus* genus.

The formulation of spores for the purpose of administering them to humans or animals is difficult and problematic since, as it involves living material, if unsuitable processes are used, there is a risk of losing a considerable portion of active principle.

Various spore-based solid compositions are known. These are prepared according to various techniques, such as, for example, lyophilization or "spray drying"; similarly, liquid suspensions of spores or simple mixtures of spores with conventional excipients are known from the pharmaceutical art, such as, for example, WO 99/49877, in which compositions of spores from lactic acid-producing bacilli are described for reducing cholesterol.

One of the main drawbacks of the prior art is the poor stability of the compositions which result therefrom, a critical factor which does not allow storage for reasonably long periods and which makes it necessary to store and conserve the composition, before it is used, at low temperatures in order to keep the properties of the spores as unaltered as possible.

Another drawback of the compositions of the prior art is the low concentration of active principle, and therefore of spores, which can be introduced into the actual composition.

Spore-based liquid compositions are available on the market, for example the suspension of bacillus spores which has been sold in Italy for a long time under the trade mark ENTEROGERMINA®. Although it is effective and has for a long time been favored by consumers, this suspension cannot contain a very high concentration of active principle (greater than 2 billion spores/5 ml).

The aim of the present invention is to provide a solid composition based on spores of nonpathogenic bacteria, hereinafter simply referred to as "spores", which is simple to produce and easy to store, and which contains a high amount of active principle and is stable over time.

It has now been found that, by adsorbing the spores onto a suitable matrix, using the fluidized air bed technique, a solid form of spores at very high concentration, which is easy to treat in industrial terms and very stable, is obtained.

In particular, it has been found that this solid form, hereinafter referred to as "composition", makes it possible to attach to the matrix a large amount of spores, creating a solid composition at high concentration, the particle size and the specific surface of which make it particularly suitable for in vivo release of the spores all along the gastrointestinal tract.

In addition, it has been found that the composition has excellent properties of fluidity and, as a result of this, it can be treated industrially for the purposes of formulating it in single-dose or multidose compositions, without it being necessary to subject it to subsequent treatments.

Thus, according to one of its aspects, the invention relates to a composition of spores of nonpathogenic bacteria of the *Bacillus* genus, adsorbed onto a matrix made up of at least one water-insoluble compound and a cellulose derivative, which can be obtained by the fluidized air bed technique.

More particularly, the invention relates to a composition of spores of nonpathogenic bacteria of the *Bacillus* genus, which can be obtained by a process which comprises treating, according to the fluidized air bed technique, a liquid suspension of said spores with a matrix made up of a water-insoluble adsorbent compound and a cellulose derivative.

According to the present invention, the expression "adsorbent compound" denotes any chemical compound, or a mixture of chemical compounds, which may be ingested and has adsorbent properties; preferably, the water-insoluble adsorbent compound is chosen from the group made up of clays, kaolin, calcium carbonate, colloidal silicas, magnesium and aluminum silicate and derivatives of cellulose and bentonite, kaolin being particularly advantageous.

According to the invention, the expression "cellulose derivative" denotes any derivative of cellulose which can be ingested, such as, for example, microcrystalline cellulose, methylcellulose, hydroxypropylmethylcellulose, etc., wide commercial ranges of which are available, microcrystalline cellulose being particularly preferred.

It is understood, even where this is not expressly indicated, that all the components of the composition of the invention are such that they may be ingested by humans and/or animals, i.e. "nontoxic". In particular, the nature and the quality of the components will be chosen according to the ultimate use of the composition and their type and purity will therefore be suitable and compatible with the final uses of the composition; consequently, by way of illustration, when the composition is intended for pharmaceutical treatment, the type and the purity of the components will have to be acceptable from a pharmaceutical point of view and so on.

The expressions "adsorbed spores", "adsorption" or "adsorb" are intended to mean, according to the present invention, retention of the spores at the surface of the matrix from which said spores are releasable in the digestive tract.

The spores can be retained on the matrix by any attachment, namely by any possible attachment (chemical, biological, physical, etc.), depending on the type of matrix used.

The relative amounts of the two components which constitute the matrix may vary within a broad range. For example, the ratio by weight of the adsorbent compound to the cellulose derivative may be between 90:10 and 10:90, preferably between 70:30 and 30:70, even more preferably between 60:40 and 40:60, the two components advantageously being present in the matrix in a ratio by weight of approximately 50:50.

In any event, the matrix of the invention is a water-insoluble mixture which is inert with respect to the spores, where the expression "inert with respect to the spores" is intended to mean that it does not negatively interfere with the spores.

The spores which may be used in the present invention are preferably spores of nonpathogenic bacteria which are particularly useful in the pharmaceutical, veterinary and/or nutrition fields. The composition of the present invention may contain spores of a single *Bacillus* or spores of various mixed Bacilli.

According to a preferred aspect, the composition of the invention comprises spores of *Bacillus subtilis* or of *Bacillus clausii*.

Preferably, the composition of the invention comprises the spores of one or more strains of *Bacillus clausii* (the prior taxonomic name of which was *Bacillus subtilis*), deposited in conformity with the Treaty of Budapest on Jan. 18, 1984 at the Collection Nationale De Cultures De Microorganismes (CNCM) of the Pasteur Institute, located at 28 Rue du Docteur Roux, 75724 PARIS Cedex 15, REPUBLIC OF FRANCE, and assigned accession numbers: I-273, I-274, I-275, and I-276.

The fluidized air bed technique well known to those skilled in the art is used to prepare the composition.

According to this technique, an aqueous suspension containing the spores, hereinafter referred to as "concentrated suspension" is sprayed onto a matrix obtained by mixing at least one adsorbent compound and a cellulose derivative, constantly agitated by a stream of air throughout the duration of the process, in a device provided for this purpose, such as, for example, a fluidized air bed granulating machine.

The concentrated suspension is aqueous, which exhibits a very high concentration of spores.

According to a particularly advantageous aspect of the invention, the concentrated suspension is obtained by inoculating one or more strains of Bacilli in a culture medium (for example based on peptones and mineral salts), incubating the mixture at a suitable temperature for 48-72 hours under aerobic conditions, separating the cells from the depleted medium with distilled water, by centrifugation, and then pasteurizing the suspension obtained. An example of such preparation is given in the experimental section.

The concentrated suspension thus prepared has a *Bacillus* spore concentration of greater than 10 billion per gram, normally between approximately 15 and approximately 25 billion per gram, or even more.

In general, the concentrated suspension is preferably conserved after having been frozen because of its high instability at ambient temperature. In this particular case, the concentrated suspension will be thawed just before its use in the process of the present invention.

Alternatively, the concentrated suspension may be an extemporaneous suspension of spores conserved in a form which is lyophilized in water.

The temperature of the stream of air used in the process of the present invention is between ambient temperature and the maximum temperature which is withstood by the spores; according to a preferred aspect, the process preferably takes place at a temperature of between 40 and 90° C., advantageously between 60 and 80° C.

Once the spraying and the adsorption of the concentrated matrix are finished, the composition obtained is subsequently kept in suspension by means of the heated stream of air until it has reached the desired residue water content, preferably until the water content is less than 3%, advantageously less than or equal to 2%.

The duration of the process is defined by the amount of concentrated suspension to be sprayed, by the rate of spraying and also by the temperature of the stream of air. Normally, for the treatment of amounts of around 30 kg of matrix, approximately two hours are necessary in order to finish the process.

The process for preparing the composition constitutes a subsequent subject of the present invention.

As indicated above, the composition of the invention may be obtained in a highly concentrated form and may have a concentration of between, for example, 3 and 30 billion spores per gram of final composition, for example between 5 and 20 billion spores per gram of final composition, advantageously of approximately 10 billion spores per gram, thus making it possible to administer consistent amounts of spores in small volumes. This important property means that the composition is particularly easy to use and, for example, can be introduced into small gel capsules or sachets or incorporated into foods or into other compositions. As needed, the composition can also be administered after having been once again suspended in water or in other suitable liquids.

The composition of the invention has proved to be stable while at the same time maintaining its titer unaltered over a long period of time, even at temperatures greater than ambient temperature (approximately 40° C.).

The determination of the spore titer of the composition of the invention can be carried out according to any procedure, for example by counting on conventional culture plates.

As indicated above, the composition of the invention has a large specific surface, by virtue of the particle size being very fine, with up to 90% of the particles of the composition having a particle size of less than or equal to 130 micrometers, preferably with 60% of the particles of the composition having a particle size of less than or equal to 60 micrometers.

In addition, the composition has no smell or taste and can thus be added to foods or drinks or to other compositions without altering their original flavor.

If desired, the composition may contain additives opportunely chosen as a function of the final consumer, of the mode of absorption or of the type of subsequent treatment to which it is desired to subject it, on the single condition that the additives are inert with respect to the spores.

For example, it will be possible to add lubricants, diluents, etc., or any other agent capable of increasing the flow thereof or of extolling other particular physical properties with the aim of facilitating the subsequent treatments of the composition.

For example, when it is desired to introduce the composition into hard gelatin capsules, it could be useful to add magnesium stearate and/or microcrystalline cellulose.

Alternatively to or jointly with the abovementioned additives, aroma-enhancing agents capable of conferring on the composition particular fragrances or flavors may be added.

The possible subsequent components may be added to the matrix before the adsorption of the spores or quite simply to the final composition obtained by the process of the invention.

As needed, the composition may be the subject of subsequent modifications; the composition may therefore be granulated according to well known techniques when it is desired to carry out compressing thereof, or may be treated so as to obtain controlled-release compositions, according to well known techniques, in order to modify the period over which it is released in the intestine.

The composition may be administered in variable amounts according to the needs for which it is administered. In general, in the case of administration to humans, it is possible to provide 10 billion spores/day and even more, advantageously from 1 to 8 billion per day, for example, 2, 4 or 6 billion spores per day, the administration being possible in a single dose or in a repeated manner.

For the purposes of its administration, the composition of the invention may, where appropriate, be formulated in dosage units; for example, by virtue of its qualities, it may be readily formulated in gelatin capsules, such as gelatin capsules in the 0, 1 or 2 format, chosen by the expert in the branch according to the dosage.

The dosage units, in the form of gel capsules or of sachets, containing the composition of the invention represent a subsequent subject of the present invention.

For example, these dosage units may contain from 1 to 10 billion of said spores, advantageously from 2 to 5 billion, from 50 to 500 mg, for example from 50 to 250 mg of kaolin and, for example, from 50 to 600 mg, for example from 50 to 300 mg of microcrystalline cellulose.

These dosage units can be administered one or more times a day, as required and depending on the concentration of the dosage unit.

For example, it is possible to prepare dosage units containing 5-7 billion spores, advantageously approximately 6 billion spores, and to administer said dosage unit just once a day.

Since it involves living material, it is obvious that the microbiological titer may undergo variations; consequently, an excess of spores of 10-20% relative to the anticipated dose is preferably added to the preparation of the composition. Given the lack of toxicity of the product, such an excess does not however cause any problems.

Some batches of the compositions of the invention packaged in glass or in polyethylene were subjected to stability studies so as to evaluate the behavior thereof at different temperatures (from 5° C. to 40° C.) and degrees of humidity (up to 75% relative humidity). The results after 24 months showed that the titer of the composition was not significantly impaired under any of the conditions tested. In addition, the resistance to antibiotics and the biochemical characteristics were evaluated under the same conditions, and were shown to be in accordance with the original properties of the product.

The composition according to the invention is useful in the pharmaceutical, veterinary and/or nutrition fields.

It in particular has the same applications as the commercially available product ENTEROGERMINA®; in particular, the composition of the invention exerts a beneficial action on the intestine and on the immune system and is particularly suitable for the treatment and prevention of intestinal dysmicrobism and endogenous dysvitaminosis and also in coadjuvant treatment in the recovery of intestinal microbial flora altered subsequent to treatment with antibiotics or to chemotherapy, as it is adapted, for example, for its use in combination with antibiotics to combat *Helicobacter pylori*.

A subject of the invention is also a medicinal product containing the composition of bacterial spores as defined above.

The examples indicated below illustrate the invention without, however, limiting it.

Preparation of the Concentrated Suspension

A prefermentation of 600 ml of a suspension of four strains of *Bacillus clausii* I-273, I-274, I-275 and I-276 (in equal proportions) at a concentration of 500 million spores/ml is carried out in 30 liters of fermentation medium for 7 hours. The prefermented suspension is inoculated into 1,000 liters of fermentation medium based on peptones and mineral salts; incubation is carried out at 37° C. for 48-72 hours under aerobic conditions, the cells are separated from the culture medium with distilled water, by centrifugation, until a final volume of 100 liters is obtained, and the suspension is pasteurized at 70° C. for 30 minutes. A concentrated suspension containing a concentration of *Bacillus clausii* spores of approximately 20 billion per gram is thus obtained.

EXAMPLE 1

15 kg of kaolin of pharmaceutical quality and 15 kg of microcrystalline cellulose of pharmaceutical quality are loaded into a system for the fluidized air bed process, and the mixture is heated for a few minutes by means of a stream of air at 60° C. Under a laminar flow hood, 15 kg of an aqueous suspension of a mixture of spores of *Bacillus clausii* I-273, I-274, I-275 and I-276 (concentrated suspension prepared as above) at a concentration of 20 billion spores per gram are loaded into a container equipped with a peristaltic pump connected to nebulization nozzles which are 1.2 mm in diameter and connected to the fluidized air bed installation. The concentrated suspension of spores is therefore sprayed onto the heated mixture with a pressure of 2 bar and a flow rate of 135 ml/minute, keeping the mixture in suspension with air at 60° C. Approximately 110 minutes later, the system is stopped, cooling is allowed to take place and the composition is recovered. A composition exhibiting the following characteristics is thus obtained:

titer—determined by counting on plates: 10 billion spores/g;
residual water content≤2%;
particle size—determined using a MALVERN® laser particle size analyzer in demineralized water: 90% of particles <100 μm, 60% of particles <50 μm;
specific surface area: 3-5 $m^2$/g.

EXAMPLE 2

Carrying out the procedure as described in example 1, but using only the *Bacillus clausii* strain I-274, a product having the following characteristics is obtained:

titer—determined by counting on plates: 10 billion spores/g;
residual water content≤2%;
particle size—determined using a MALVERN® laser particle size analyzer in demineralized water: 90% of particles <130 μm, 60% of particles <60 μm;
specific surface area: 3.5-5 $m^2$/g.

EXAMPLE 3

Carrying out the procedure as described in example 1, but using only the *Bacillus clausii* strain I-276, a product having the following characteristics is obtained:

titer of 12 billion spores/g;
residual water content≤3%;
particle size—determined using a MALVERN® laser particle size analyzer in demineralized water: 90% of particles <130 μm, 60% of particles <60 μm;
specific surface area: 3-5 $m^2$/g.

EXAMPLE 4

57 g of microcrystalline cellulose and 3 g of magnesium stearate are added to 240 g of a composition of example 1. After having been mixed, the composition thus obtained is distributed into format 1 hard gelatin operculated capsules, each containing 300 mg of the following composition:

| | |
|---|---|
| Matrix (kaolin + microcrystalline cellulose) containing approximately 2 billion spores of *Bacillus clausii* (I-273, I-274, I-275, I-276) | mg 240.00 |
| Microcrystalline cellulose | mg 57.00 |
| Magnesium stearate | mg 3.00 |

EXAMPLE 5

Format 1 Hard Gelatin Capsules Containing 275 mg of Composition

| | |
|---|---|
| Matrix (kaolin + microcrystalline cellulose) containing approximately 2 billion spores of *Bacillus clausii* (I-273, I-274, I-275, I-276) | mg 200.00* |
| Microcrystalline cellulose | mg 72.25 |
| Magnesium stearate of plant origin | mg 2.75 |

(*in the production formula 220.00 mg corresponding to a 10% overdose)

EXAMPLE 6

Format 1 Hard Gelatin Capsules Containing 255 mg of Composition

| | |
|---|---|
| Matrix (calcium carbonate + microcrystalline cellulose) containing approximately 2 billion spores of *Bacillus clausii* (I-273, I-274, I-275, I-276) | mg 200.00* |
| Microcrystalline cellulose | mg 52.25 |
| Magnesium stearate of plant origin | mg 2.75 |

(*in the production formula 220.00 mg corresponding to a 10% overdose)

The invention claimed is:

1. A composition comprising live spores of nonpathogenic bacteria of the *Bacillus* genus obtained by applying a liquid suspension of the live spores onto a matrix of a water-insoluble adsorbent compound and a cellulose derivative using a fluidized air bed technique.

2. The composition of claim 1, wherein the cellulose derivative is microcrystalline cellulose.

3. The composition of claim 1, wherein the adsorbent compound is selected from the group consisting of kaolin and calcium carbonate.

4. The composition of claim 1, wherein the ratio by weight of the adsorbent compound to the cellulose derivative is between 90:10 and 10:90.

5. The composition of claim 4, wherein the ratio is between 70:30 and 30:70.

6. The composition of claim 5, wherein the ratio is approximately 50:50.

7. The composition of claim 1, wherein the composition is in the form of a dosage unit in gel capsules or sachets.

8. The composition of claim 7, wherein each dosage unit contains from 1 to 10 billion live spores, from 50 to 500 mg of kaolin, and from 50 to 600 mg of microcrystalline cellulose.

9. The composition of claim 8, wherein each dosage unit contains from 2 to 5 billion live spores, from 50 to 250 mg of kaolin, and from 50 to 300 mg of microcrystalline cellulose.

10. The composition of claim 7, wherein each dosage unit contains approximately 2 billion live spores in gel capsules.

11. The composition of claim 7, wherein each dosage unit contains approximately 6 billion live spores in gel capsules.

12. The composition of claim 1, wherein the live spores are live spores of *Bacillus subtilis* or *Bacillus clausii*.

13. The composition of claim 1, wherein the live spores originate from one or more strains of *Bacillus clausii* that are deposited in the Collection Nationale De Cultures De Microorganisms of the Institut Pasteur under accession numbers I-273, I-274, I-275, and I-276.

14. The composition of claim 1, wherein the composition contains from 3 to 30 billion live spores per gram of composition.

15. The composition of claim 14, wherein the composition contains from 5 to 20 billion live spores per gram of composition.

16. The composition of claim 15, wherein the composition contains approximately 10 billion live spores per gram of composition.

* * * * *